(12) United States Patent
Kraft

(10) Patent No.: US 8,344,023 B2
(45) Date of Patent: Jan. 1, 2013

(54) 2,5-DI- AND 2,2,5-TRISUBSTITUTED DI- AND TETRAHYDROFURAN DERIVATIVES AND THEIR USE FOR THE PRODUCTION OF PERFUMES

(75) Inventor: Philip Kraft, Duebendorf (CH)

(73) Assignee: Givaudan SA, Vernier (CH)

( * ) Notice: Subject to any disclaimer, the term of this patent is extended or adjusted under 35 U.S.C. 154(b) by 291 days.

(21) Appl. No.: 12/602,275

(22) PCT Filed: Jun. 3, 2008

(86) PCT No.: PCT/CH2008/000249
§ 371 (c)(1),
(2), (4) Date: Nov. 30, 2009

(87) PCT Pub. No.: WO2008/148236
PCT Pub. Date: Dec. 11, 2008

(65) Prior Publication Data
US 2010/0173999 A1 Jul. 8, 2010

(30) Foreign Application Priority Data
Jun. 5, 2007 (GB) .................................. 0710700.6

(51) Int. Cl.
*A61K 31/341* (2006.01)
*C07D 307/28* (2006.01)
(52) U.S. Cl. ........................................ 514/461; 549/507
(58) Field of Classification Search .................. 514/461; 549/507
See application file for complete search history.

(56) References Cited

U.S. PATENT DOCUMENTS
5,591,874 A 1/1997 Puckette et al.

FOREIGN PATENT DOCUMENTS
| | | |
|---|---|---|
| CH | 611624 A5 | 6/1979 |
| CH | 685390 A5 | 6/1995 |
| EP | 0010142 A | 4/1980 |
| EP | 0131254 A | 1/1985 |
| JP | 11349581 A | 12/1999 |
| WO | 9113882 A1 | 9/1991 |
| WO | 9935137 A1 | 7/1999 |
| WO | 2005087756 A | 9/2005 |

OTHER PUBLICATIONS

English Language Abstract for CH685390 taken from esp@cenet.com, Jun. 30, 1995.
English Language Abstract for CH611624 taken from esp@cenet.com, Jun. 15, 1979.
English Language Abstract for EP001042 taken from esp@cenet.com, Apr. 30, 1980.
English Language Abstract for EP0131254 taken from esp@cenet.com, Jan. 16, 1985.
English Language Abstract for JP11349581 taken from esp@cenet.com, Dec. 21, 1999.

*Primary Examiner* — Taofiq A Solola
(74) *Attorney, Agent, or Firm* — Norris McLaughlin & Marcus PA

(57) ABSTRACT

Di-/trisubstituted furans of the formula (I) and their use as odorants wherein $R^1$ is hydrogen or methyl; $R^2$ is ethyl, propyl or isopropyl; the bond between C-3 and C-4 is a single bond, or the dotted line together with the bond between C-3 and C-4 represents a double bond; and the bond between C-4' and C-5' is a single bond, or the dotted line together with the bond between C-4' and C-5' represents a double bond, either in (E)- or (Z)-configuration. The invention furthermore relates to a method of their production and to perfume compositions comprising them.

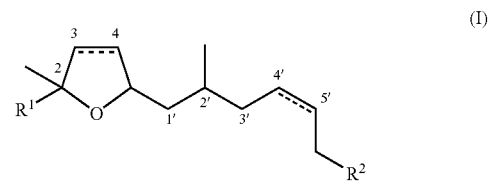

(I)

5 Claims, No Drawings

2,5-DI- AND 2,2,5-TRISUBSTITUTED DI- AND TETRAHYDROFURAN DERIVATIVES AND THEIR USE FOR THE PRODUCTION OF PERFUMES

This is an application filed under 35 USC 371 of PCT/CH2008/000249.

The present invention relates to di-/trisubstituted furans, namely 2-methyl-substituted 5-(2'-methylalk-4'-enyl)-2,5-dihydro-/tetrahydrofurans and 2-methyl-substituted 5-(2'-methylalkyl)-2,5-dihydro-/tetrahydrofurans, and their use as odorants. This invention relates furthermore to a method of their production, and to perfume compositions comprising them.

In the fragrance industry there is a constant demand for new compounds that enhance, to modify or improve on odour notes. So-called "soliflores", reconstitutions and interpretations of single-flower notes, marked the beginning of the art of perfumery, and floral accords still form the central part of the perfumer's palette. Almost half of all perfumes sold over the counter still have one predominant floral or flowery note, for example jasmin, rose, honeysuckle, lilac or lily of the valley.

Surprisingly, we now found a new class of compounds constituting new floral odorants by combining common floral notes with fruity, often in the direction of citrus fruits, or fruity-spicy tonalities, and a more or less pronounced green freshness, which altogether amounts to a highly desirable sparkling effect, while still being long-lasting and transparent in use. This interplay of floral and fruity notes in one single compound generates a unique sparkling effect, which is underscored by more or less pronounced green nuances conveying additional freshness.

Thus, the present invention refers in one of its aspects to a compound of formula (I)

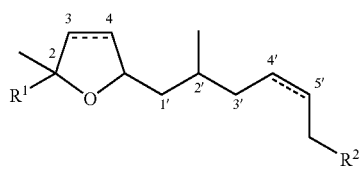

(I)

wherein
$R^1$ is hydrogen or methyl;
$R^2$ is ethyl, propyl or isopropyl;
the bond between C-3 and C-4 is a single bond, or the dotted line together with the bond between C-3 and C-4 represents a double bond; and
the bond between C-4' and C-5' is a single bond, or the dotted line together with the bond between C-4' and C-5' represents a double bond, either in (E)- or (Z)-configuration.

The compounds of formula (I) wherein the dotted line together with the bond between C-3 and C-4 represents a double bond, and the bond between C-4' and C-5' is a single bond, or the dotted line together with the bond between C-4' and C-5' represents a double bond represent particular aspects of the invention.

Another aspect of the invention refers to compounds of formula (I) wherein the bond between C-3 and C-4 is a single bond, and the bond between C-4' and C-5' is a single bond, or the dotted line together with the bond between C-4' and C-5' represents a double bond.

Particularly preferred compounds of formula (I) are (4'Z)-2,2-dimethyl-5-(2'-methyloct-4'-enyl)-2,5-dihydrofuran, 2,2-dimethyl-5-(2'-methyloctyl)tetrahydrofuran, (4'Z)-2-methyl-5-(2'-methyloct-4'-enyl)tetrahydrofuran and 2-methyl-5-(2-methyloctyl)tetrahydrofuran.

The compounds of formula (I) may be used alone or in admixture with other fragrances selected from the extensive range of natural and synthetic molecules, such as ethereal oils and extracts, alcohols, aldehydes and ketones, ethers and acetals, esters and lactones, macrocycles and heterocycles.

The following list comprises a few illustrative examples of known fragrances, which harmonize equally well with the compounds of the present invention:

Ethereal oils and extracts, e.g. bergamot oil, coriander oil, galbanum oil, geranium oil, jasmin absolute, lemon oil, lime oil, neroli oil, oak moss absolute, patchouli oil, petitgrain oil, rose oil, sandalwood oil or ylang-ylang oil;

Alcohols, e.g. citronellol, dihydromyrcenol, Ebanol®, eugenol, geraniol, linalool, phenylethyl alcohol, Sandelore®, Super Muguet®, terpineol or Timberol®;

Aldehydes and ketones, e.g. α-amylcinnamaldehyde, decanal, Hedione®, hydroxycitronellal, isoeugenol, Iso E Super®, Isoraldeine®, methyl ionone or vanillin;

Ether and acetals, e.g. Ambrofix®, geranyl methyl ether, Magnolan®, rose oxide or Spirambrene®

Esters and lactones, e.g. ambrettolide, benzyl acetate, benzyl salicylate, coumarin, γ-decalactone, ethylene brassylate, Serenolide®, Thibetolide®, γ-undecalactone or vetivenyl acetate;

Heterocycles, e.g. galbazine, indol, isobutylchinoline.

Due to their unique fruity-floral character, the compounds of formula (I) are especially well suited for use as transparent fresh, floral-fruity notes in the heart of feminine fine fragrances, unisex colognes, or in compositions for laundry- or home-care applications.

In addition to their admixture with other fragrances, the compounds of the present invention may be admixed with one or more ingredients or excipients conventionally used in conjunction with fragrances in perfume compositions, for example carrier materials, and other auxiliary agents commonly used in the art, e.g., solvents such as dipropylene glycol (DPG), isopropyl myristate (IPM), and triethyl citrate (TEC).

The compounds of the present invention may be used in a broad range of fragrance applications, e.g. in any field of fine and functional perfumery, such as perfumes, household products, laundry products, body care products and cosmetics. The compounds can be employed in widely varying amounts, depending upon the specific application and on the nature and quantity of other fragrances. The proportions in which the compounds of the present invention are employed in application may vary within a large range of values and will depend upon the nature of the applications one intends to perfume, for example the nature of co-ingredients, and the particular effect that the perfumer seeks. Generally however, one may employ up to about 30% by weight in fine fragrances, e.g. from about 5% by weight to about 15% by weight, and up to about 50% by weight based on the perfume composition in other fragrance applications, e.g. laundry products. However, these values are given only by way of example, since the experienced perfumer may also achieve effects or may create novel accords with lower or higher concentrations.

The compounds of the present invention may be employed into the fragrance application simply by directly mixing the perfume composition with the fragrance application, or they may, in an earlier step, be entrapped with an entrapment material such as polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the application.

Thus, the invention additionally provides a method of manufacturing a fragrance application and consumer products resulting therefrom. The method comprises the incorporation therein of a compound of formula (I) as a fragrance ingredient, either by directly admixing the compound to the application or by admixing a perfume composition comprising a compound of formula (I), which may then be mixed to a fragrance application, using conventional techniques and methods. Through the addition of an olfactory acceptable amount of a compound of the present invention, or a mixture thereof, the odour notes of a fragrance application will be improved, enhanced or modified.

Thus, the invention furthermore provides a method for improving, enhancing or modifying a fragrance application through the addition thereto of an olfactory acceptable amount of a compound of formula (I), or a mixture thereof.

The invention also provides a fragrance application comprising:
a) as odorant a compound of formula (I) or a mixture thereof; and
b) a consumer product base.

As used herein, "fragrance application" means any products, such as fine fragrances, e.g. eaux de perfume and eaux de toilette; household products, e.g. detergents for dishwasher, surface cleaner, air freshener; laundry products, e.g. softener, bleach, detergent; body care products, e.g. after-shave lotion, shampoo, shower gel, shower and bath salt, hygiene product; and cosmetics, e.g. deodorants, vanishing creams, comprising an odorant. This list of products is given by way of illustration and is not to be regarded as being in any way limiting.

Compounds of formula (I) may be prepared by Wittig reaction of 3-methyl-5-oxopentyl acetate with $C_3$-$C_5$ alkyl triphenylphosphonium halides, and subsequent saponification resulting in 3-methyl substituted alk-5-enals. By reaction of these 3-methylalk-5-enals with Grignard reagents of but-3-yn-2-ol and 2-methylbut-3-yn-2-ol, respectively, double-unsaturated 1,4-diols are accessible, which can be cyclized to 2-methyl-substituted 5-(2'-methylalk-4'-enyl)-2,5-dihydrofurans by means of common dehydration reagents, such as potassium hydrogen sulphate. Hydrogenation then leads to the corresponding tetrahydrofurans, while selective hydrogenation of the triple bond on the alkyne diol stage, for instance by prolonged Lindlar hydrogenation, or hydrogenation of the double on the 3-methylalk-5-enal stage, allows the synthesis of all double-bond permutations covered by the general formula (I). Thus, the double bonds can be selectively placed. By modification of the condition of the Wittig reaction, the stereochemistry of the $\Delta^4$-double bond in the side chain can also be controlled. This as well as the synthesis or resolution of specific enantiomers or diastereoisomers is general state of the art; the general formula comprises not only all double-bond isomers, but also all possible enantiomeric and diastereomeric compositions. Due to simple cost constraints, the preparation of diastereoisomeric mixtures with (Z)-configured double bonds is, however, generally advantageous.

The invention is now further described with reference to the following non-limiting examples. These examples are for the purpose of illustration only and it is understood that variations and modifications can be made by one skilled in the art. The NMR data are given relative to TMS standard.

EXAMPLE 1

(4'Z)-2,2-Dimethyl-5-(2'-methyloct-4'-enyl)-2,5-dihydrofuran

Under an atmosphere of nitrogen, a solution of 46.3 g (413 mmol) of potassium tert-butoxide in 250 mL of dry THF was a added between −15° C. and −10° C. to a stirred mixture of 150 g (376 mmol) butyl triphenylphosphonium bromide in 500 mL of dry THF. After complete addition, stirring was continued at −10° C. for 30 min, prior to the dropwise addition of 65.3 g (413 mmol) of 3-methyl-5-oxopentyl acetate in 250 mL of dry THF within a period of 30 min. Stirring was continued a further 15 min at −10° C., before the cooling bath was removed and the reaction mixture was allowed to warm to room temp. After 3 h of stirring at room temp., the reaction mixture was poured into 1 L of water, the organic layer separated and aqueous one extracted twice with 1 L of ether each. The combined organic extracts were washed with water and brine, dried with sodium sulphate, and concentrated under reduced pressure. The crude material (191 g) was purified by flash chromatography (1.00 kg of silica gel, pentane/ether, 19:1, $R_f$=0.40) to afford 57.9 g (78%) of (5Z)-3-methylnon-5-enyl acetate as a colourless liquid.

In the next step, 55.0 g (278 mmol) of this (5Z)-3-methylnon-5-enyl acetate was dissolved in 600 mL of a 1:1 mixture of ethanol and water. With vigorous stirring, 55.5 g (1.39 mol) of sodium hydroxide was added, and the reaction mixture was subsequently heated to reflux for 3 h. After the reaction mixture had cooled to room temp., the ethanol was removed in a rotary evaporator under reduced pressure, and the resulting residue diluted with 300 mL of water. The crude product was extracted twice with 500 mL of ether each, and the combined organic extracts were washed twice with 300 mL of brine. After drying with sodium sulphate and removal of the solvent under reduced pressure, the resulting residue (51.2 g) was purified by flash chromatography (1.00 kg of silica gel, pentane/ether, 9:1, $R_f$=0.11) to provide 39.9 g (92%) of (5Z)-3-methylnon-5-en-1-ol as a colourless liquid.

A solution of 10.4 g (95.6 mmol) of ethyl bromide in 40 mL of dry tetrahydrofuran was added dropwise over a period of 30 min to a vigorously stirred suspension of 2.32 g (95.6 mmol) of magnesium turnings in 15 mL of dry tetrahydrofuran, with the reaction being initiated by occasional heating with a heat gun. After stirring the reaction mixture for 90 min under reflux, it was allowed to cool down to room temp., and a solution of 3.54 g (42.2 mmol) of 2-methylbut-3-yn-2-ol in 40 mL of dry tetrahydrofuran was added dropwise with stirring. The reaction mixture was then again refluxed for 3 h, the heating bath removed and a solution of 6.50 g (42.2 mmol) of (5Z)-3-methylnon-5-en-1-ol in 40 mL of dry tetrahydrofuran added at room temp. with stirring over a period of 30 min. The reaction mixture was refluxed with stirring overnight, allowed to cool to room temp., and quenched by pouring into 100 mL of an aqueous satd. NH$_4$Cl solution. The organic layer was separated, and the aqueous one extracted three times with 500 mL of ether each. The combined organic extracts were dried with sodium sulphate, and concentrated to dryness in a rotary evaporator. The resulting residue (10.8 g) was purified by flash chromatography (200 g of silica gel, pentane/ether, 1:1, $R_f$=0.22) to furnish 7.76 g (77%) of (9Z)-2,7-dimethyltridec-9-en-3-yne-2,5-diol as a colourless oil.

At room temp., 520 mg (0.488 mmol) of 10% palladium on barium sulphate and 190 mg (1.47 mmol) of quinoline were added to a stirred solution of 7.70 g (32.3 mmol) of this (9Z)-2,7-dimethyltridec-9-en-3-yne-2,5-diol in 170 mL of ethanol. The flask was evacuated and flushed with nitrogen three times, and three times evacuated and flushed with hydrogen. The resulting reaction mixture was then stirred for 1.5 h under an atmosphere of hydrogen at ambient pressure and temperature, prior to evacuation and ventilation with nitrogen. The reaction flask was opened to air, and the catalyst filtered off by suction over a pad of Celite. After removal of the solvent in a rotary evaporator under reduced pressure, the resulting crude product (8.07 g) was purified by flash chromatography (100 g of silica gel, pentane/ether, 1:1, $R_f$=0.28) to afford 4.28 g (55%) of (3Z,9Z)-2,7-dimethyltrideca-3,9-diene-2,5-diol as a colorless oil.

In a Kugelrohr distillation apparatus 4.20 g (17.5 mmol) of (3Z,9Z)-2,7-dimethyltrideca-3,9-diene-2,5-diol and 300 mg (2.21 mmol) of $KHSO_4$ were heated to 150° C. at 120 mbar, with trapping the evaporating reaction product in a bulb at −78° C. The temperature was gradually increased to 180° C. until no further material condensed in the cold trap. The resulting distillate (2.27 g) was purified by flash chromatography (200 g of silica-gel, pentane/ether, 99:1, $R_f$=0.66 for pentane/ether, 19:1) to furnish 2.14 g (55%) of the title compound. Further purification by Kugelrohr distillation provided at 70-80° C./0.05 mbar 1.14 g (29%) of (4'Z)-2,2-dimethyl-5-(2'-methyloct-4'-enyl)-2,5-dihydrofuran as a colourless liquid diastereomeric mixture.

IR (film): ν=1174/1029/1099 (ν C—O—C), 1377/1359/1364 ($δ_s$ $CH_3$), 1459 ($δ_{as}$ $CH_3$), 963 (δ C=C—H), 1717 (ν C=C, ring) $cm^{-1}$.—$^1H$ NMR ($CDCl_3$): δ=0.90 (t, J=7.5 Hz, 3H, 8'-$H_3$), 0.93 (d, J=7.0 Hz, 3H, 2'-Me), 1.28/1.32 (2s, 6H, 2-$Me_2$), 1.36 (q, J=7.5 Hz, 2H, 7'-$H_2$), 1.43-1.60 (m, 2H, 1'-$H_2$), 1.65-1.77 (m, 1H, 2'-H), 1.90-2.10 (m, 4H, 3'-,6'-$H_2$), 4.87 ($m_c$, 1H, 5-H), 5.34-5.45 (m, 2H, 4'-,5'-H), 5.65-5.73 (m, 2H, 3,4-H).—$^{13}C$ NMR ($CDCl_3$): δ=13.8/13.8 (2q, C-8'), 19.7/20.2 (2q, 2'-Me), 22.8/22.8 (2t, C-7'), 27.9/28.0 (2q, 2-$Me_{ax}$), 29.4/29.4 (2t, C-6'), 29.4/29.5 (2q, 2-$Me_{eq}$), 30.2/30.5 (2d, C-2'), 34.7/35.1 (2t, C-3'), 44.3/44.5 (2t, C-1'), 83.2/83.6 (2d, C-5), 86.8/86.9 (2s, C-2), 128.0/128.2/128.4/128.8 (4d, C-4',-5'), 130.6/130.8 (2d, C-4), 135.0/135.1 (2d, C-3).-MS (EI): m/e (%)=41 (27) [$C_3H_5^+$], 55 (15) [$C_4H_7^+$], 69 (11) [$C_5H_9^+$]81 (11) [$C_6H_9^+$], 97 (100) [$C_6H_9O^+$], 109 (4) [$C_7H_9O^+$], 137 (32) [$C_9H_{13}O^+$], 165 (6) [$C_{11}H_{17}O^+$], 179 (2) [$M^+$—$CH_3$—$C_2H_4$], 189 (1) [$M^+$—$CH_3$—$H_2O$], 207 (6) [$M^+$—$CH_3$], 222 (1) [$M^+$].

Odour description: sweet, fruity-floral note with some reminiscence to jasmine and blackcurrant, and additional sparkling green accents.

EXAMPLE 2

2,2-Dimethyl-5-(2'-methyloctyl)tetrahydrofuran

At room temp., a stirred suspension 100 mg (0.95 mmol) of 10% palladium on charcoal and 500 mg (2.25 mmol) of (4'Z)-2,2-dimethyl-5-(2'-methyloct-4'-enyl)-2,5-dihydrofuran in 10.0 mL of ethyl acetate was thrice evacuated and flushed with nitrogen. Following three further cycles of evacuation and flushing with hydrogen, the reaction mixture was vigorously stirred at room temp. overnight under a positive pressure of hydrogen. The reaction flask was then evacuated again, flushed with nitrogen, and opened to air. The catalyst was removed by vacuum filtration over a pad of Celite, and the filtrate concentrated in a rotary evaporator. The resulting residue (590 mg) was purified by Kugelrohr distillation to furnish at 90-115° C./0.5 mbar 450 mg (88%) of 2,2-dimethyl-5-(2'-methyloctyl)tetrahydrofuran as a colorless odoriferous liquid.

IR (film): ν=1139/1043 (ν C—O—C), 1460 ($δ_{as}$ $CH_3$), 1377/1364 ($δ_s$ $CH_3$) $cm^{-1}$,—$^1H$ NMR ($CDCl_3$): δ=0.87 (t, J=6.5 Hz, 3H, 8'-$H_3$), 0.89 (d, J=6.5 Hz, 3H, 2'-Me), 1.22/1.24 (2s, 6H, 2-$Me_2$), 1.25-1.29 (m, 6H, 3'-$H_2$-5'-$H_2$), 1.30-160 (m, 7H, 1'-,6'-,7'-,7'-$H_2$, 2'-H), 1.69-1.74 (m, 3H, 3-$H_2$, 4-$H_b$), 2.01 ($m_c$, 1H, 4-$H_a$), 4.02 ($m_c$, 1H, 5-H).—$^{13}C$ NMR ($CDCl_3$): δ=14.1/14.1 (2q, C-8'), 19.8/20.0 (2q, 2'-Me), 22.7/22.7 (2t, C-7'), 26.8/26.8 (2t, C-4'), 28.2/28.2/29.4/29.4 (4q, 2-$Me_2$), 29.6/29.6 (2t, C-5'), 30.0/30.3 (2d, C-2'), 31.8/31.9 (2t, C-6'), 32.2/32.6 (2t, C-4), 37.4/37.5 (2t, C-3'), 38.6/38.6 (2t, C-3), 44.0/44.3 (2t, C-1'), 76.7/77.0 (2d, C-5), 79.9/80.0 (2s, C-2).-MS (EI): m/e (%)=43 (38) [$C_3H_7^+$], 55 (21) [$C_4H_7^+$], 70 (11) [$C_5H_{10}^+$], 81 (52) [$C_6H_9^+$], 99 (100) [$C_6H_{11}O^+$], 109 (3) [$C_7H_9O^+$], 193 (2) [$M^+$—$CH_3$—$H_2O$], 211 (5) [$M^+$—$CH_3$].—

Odour description: sweet, fruity-floral note, with some reminiscence to roses and grapefruit, and a sparkling green-metallic freshness.

EXAMPLE 3

(4'Z)-2-Methyl-5-(2'-methyloct-4'-enyl)tetrahydrofuran

A solution of 10.4 g (95.6 mmol) of ethyl bromide in 40 mL of dry tetrahydrofuran was added dropwise over a period of 30 min to a vigorously stirred suspension of 2.32 g (95.6 mmol) of magnesium turnings in 15 mL of dry tetrahydrofuran, with the reaction being initiated by occasional heating with a heat gun. After stirring the reaction mixture for 90 min under reflux, it was allowed to cool down to room temp., and a solution of 2.95 g (42.1 mmol) of but-3-yn-2-ol in 40 mL of dry tetrahydrofuran was added dropwise with stirring. The reaction mixture was then again refluxed for 3 h, the heating bath removed and a solution of 6.50 g (42.2 mmol) of (5Z)-3-methylnon-5-en-1-ol (vide supra) in 40 mL of dry tetrahydrofuran added at room temp. with stirring over a period of 30 min. The reaction mixture was refluxed with stirring overnight, allowed to cool to room temp., and quenched by pouring into 100 mL of an aqueous satd. $NH_4Cl$ solution. The organic layer was separated, and the aqueous one extracted three times with 500 mL of ether each. The combined organic extracts were dried with sodium sulphate, and concentrated to dryness in a rotary evaporator. The resulting residue (8.85 g) was purified by flash chromatography (200 g of silica gel, pentane/ether, 1:1, $R_f$=0.21) to furnish 7.71 g (82%) of (9Z)-7-methyltridec-9-en-3-yne-2,5-diol as a colourless oil.

At room temp., 550 mg (0.516 mmol) of 10% palladium on barium sulphate and 200 mg (1.55 mmol) of quinoline were added to a stirred solution of 7.60 g (33.9 mmol) of this (9Z)-7-methyltridec-9-en-3-yne-2,5-diol in 170 mL of ethanol. The flask was evacuated and flushed with nitrogen three times, and three times evacuated and flushed with hydrogen. The resulting reaction mixture was then stirred for 2 h under an atmosphere of hydrogen at ambient pressure and temperature, prior to evacuation and ventilation with nitrogen. The reaction flask was opened to air, and the catalyst filtered off by suction over a pad of Celite. After removal of the solvent in a rotary evaporator under reduced pressure, the resulting crude product (6.87 g) was purified by flash chromatography (100 g of silica gel, pentane/ether, 1:1, $R_f$=0.10) to afford 6.15 g (80%) of (9Z)-7-methyltrideca-9-ene-2,5-diol as a colorless oil.

In a Kugelrohr distillation apparatus 6.15 g (26.9 mmol) of (9Z)-7-methyltrideca-9-ene-2,5-diol and 270 mg (1.99 mmol) of KHSO$_4$ were heated to 150° C. at 120 mbar, with trapping the evaporating reaction product in a bulb at −78° C. The temperature was gradually increased to 180° C. until no further material condensed in the cold trap. The resulting distillate (5.82 g) was purified by flash chromatography (200 g of silica-gel, pentane/ether, 99:1, R$_f$=0.58 for pentane/ether, 19:1) to furnish the title compound. Further purification by Kugelrohr distillation provided at 95-150° C./31 mbar 4.51 g (80%) of (4'Z)-2-methyl-5-(2'-methyloct-4'-enyl)tetrahydrofuran as a colourless odoriferous liquid.

IR (film): ν=1091 (ν C—O—C), 1376 (δ$_s$ CH$_3$), 968 (δ C=C—H), 1458 (δ$_{as}$ CH$_3$) cm$^{-1}$.—$^1$H NMR (CDCl$_3$): δ=0.87 (d, J=7.0 Hz, 3H, 2'-Me), 0.90 (t, J=7.0 Hz, 3H, 8'-H$_3$), 1.21/1.23 (2d, J=6.5 Hz, 3H, 2-Me), 1.37 (q, J=7.5 Hz, 2H, 7'-H$_2$), 1.40 (m$_c$, 2H, 1'-H$_2$), 1.42-1.70 (m, 3H, 3-,4-H$_b$, 2'-H), 1.83-2.10 (m, 6H, 3'-,6'-H$_2$), 3.91 (m$_c$, 1H, 2-H), 4.08 (m$_c$, 1H, 5-H), 5.33-5.44 (m, 2H, 4'-,5'-H).—$^{13}$C NMR (CDCl$_3$): δ=13.6/13.8/13.8/14.1 (4q, C-8'), 19.4/19.5/19.8/20.0 (4q, 2'-Me), 21.3/21.4/21.5/21.5 (4q, 2-Me), 22.6/22.7/22.8/22.8 (4t, C-7'), 29.4/29.4/29.4/29.4 (4t, C-6'), 30.8/30.9/31.1/31.6 (4d, C-2'), 31.9/32.0/32.7/32.8/32.9/33.0/33.8/33.9 (8t, C-3,-4), 34.6/34.7/34.9/35.0 (4t, C-3'), 42.8/43.0/43.1/43.5 (4t, C-1'), 74.1/74.2/74.9/75.0/76.5/77.0/77.5/77.9 (8d, C-2,-5), 128.1/128.3/128.5/128.6/130.6/130.8/131.7/131.9 (8d, C-4',-5').-MS (EI): m/e (%)=41 (53) [C$_3$H$_5$$^+$], 55 (40) [C$_4$H$_7$$^+$], 68 (32) [C$_8$H$_{14}$$^+$—C$_3$H$_6$], 81 (38) [C$_8$H$_{14}$$^+$—C$_2$H$_5$], 85 (61) [C$_5$H$_9$O$^+$], 95 (12) [C$_8$H$_{14}$$^+$—CH$_3$], 98 (11) [C$_6$H$_{10}$O$^+$], 110 (41) [C$_8$H$_{14}$$^+$], 125 (100) [C$_8$H$_{13}$O$^+$], 167 (1) [M$^+$—C$_3$H$_7$], 181 (1) [M$^+$—C$_2$H$_5$], 195 (4) [M$^+$—CH$_3$], 210 (1) [M$^+$].

Odour description: sweet, fruity-floral note with some reminiscence to lilac, lily of the valley, and coriander, and a prominent fresh green tonality.

EXAMPLE 4

2-Methyl-5-(2-methyloctyl)tetrahydrofuran

At room temp., a stirred suspension 150 mg (1.43 mmol) of 10% palladium on charcoal and 1.50 g (7.13 mmol) of (4'Z)-2-methyl-5-(2'-methyloct-4'-enyl)tetrahydrofuran in 15.0 mL of ethyl acetate was evacuated three times with subsequent flushing with nitrogen. Following three further cycles of evacuation and flushing with hydrogen, the reaction mixture was vigorously stirred at room temp. overnight under a hydrogen atmosphere. The reaction flask was then evacuated again, flushed with nitrogen, and opened to air. The catalyst was removed by vacuum filtration over a pad of Celite, and the filtrate concentrated in a rotary evaporator. The resulting residue (1.51 g) was purified by Kugelrohr distillation to furnish at 45-55° C./0.5 mbar 1.45 g (96%) of 2-methyl-5-(2'-methyloctyl)tetrahydrofuran as a colorless odoriferous liquid.

IR (film): ν=1091/1010 (ν C—O—C), 1375 (δ$_s$ CH$_3$), 1459 (δ$_{as}$ CH$_3$) cm$^{-1}$.—$^1$H NMR (CDCl$_3$): δ=0.88 (t, J=7.0 Hz, 3H, 8'-H$_3$), 0.89 (d, J=7.0 Hz, 3H, 2'-Me), 1.11-1.37 (m, 12H, 1'-H$_2$, 3'-H$_2$-7'-H$_2$), 1.21/1.23 (2d, J=7.0 Hz, 3H, 2-Me), 1.46 (m$_c$, 2H, 3-,4-H$_b$), 1.59 (m$_c$, 1H, 2'-H), 1.94-2.08 (m, 2H, 3-,4-H$_a$), 3.90 (m$_c$, 1H, 2-H), 4.07 (m$_c$, 1H, 5-H).—$^{13}$C NMR (CDCl$_3$): δ=14.1/14.1/14.1/14.1 (4q, C-8'), 19.6/19.7/20.0/20.1 (4q, 2'-Me), 21.3/21.4/21.5/21.5 (4q, 2-Me), 22.7/22.7/22.7/22.7 (4t, C-7'), 26.8/26.8/26.8/26.8 (4t, C-4'), 29.6/29.6/29.6/29.6 (4t, C-5'), 30.0 301/30.3/30.5 (4d, C-2'), 31.9/31.9/31.9/31.9 (4t, C-6'), 31.6/32.0/32.7/32.8/32.9/33.0/33.9/34.0 (8t, C-3,-4), 37.3/37.4/37.5/37.6 (4t, C-3'), 43.5/43.6/43.8/43.9 (4t, C-1'), 74.1/74.2/74.9/75.0 (4d, C-5), 76.6/77.0/77.6/78.0 (4d, C-2).-MS (EI): m/e (%)=41 (18) [C$_3$H$_5$$^+$], 57 (12) [C$_5$H$_9$O$^+$—C$_2$H$_4$], 67 (10) [C$_5$H$_9$O$^+$—H$_2$O], 85 (100) [C$_5$H$_9$O$^+$], 194 (1) [M$^+$—H$_2$O], 212 (1) [M$^+$].

Odour description: sweet, fruity-floral note, reminiscent of jasmine and citrus fruits with a fresh, green-sparkling background.

EXAMPLE 5

Unisex Fine Fragrance

| Compound/Ingredient | parts by weight 1/1000 |
|---|---|
| Ambrettolide ((10E)-oxacycloheptadec-10-en-2-one) | 14 |
| AMBROFIX ™ ((3aR,5aS,9aS,9bR)-dodecahydro-3a,6,6,9a-tetramethylnaphtho[2,1-b]furan) | 65 |
| CASHMERAN ™ (1,2,3,5,6,7-hexahydro-1,1,2,3,3-pentamethyl 4H-inden-4-one) | 25 |
| Coumarin | 10 |
| delta-Decalactone | 25 |
| Diethyl phthalate | 180 |
| Dipropylene glycol (DPG) | 80 |
| Ethylene brassylate | 160 |
| GEORGYWOOD ™ ((Z)-1-(1,2,3,4,5,6,7,8-octahydro-1,2,8,8-tetramethylnaphthalen-2-yl)ethanone) | 55 |
| (3Z)-Hex-3-enyl benzoate at 10% in DPG | 25 |
| ISO E SUPER ™ (1-(2',3',8',8'-tetramethyl-1',2',3',4',5',6',7',8'-octahydronaphthalen-2'-yl)ethanone) | 100 |
| Lilial (3-(4-tert-butylphenyl)-2-methylpropanal) | 25 |
| Neroline (2-Ethoxy naphthalene) | 3 |
| Orris butter at 10% in DPG | 25 |
| Prunolide (gamma-Nonalactone) | 8 |
| Tropional (2-Methyl-(1',3'-benzodioxol-5-yl)propanal) | 35 |
| UNDECAVERTOL ™ (4-Methyldec-3-en-5-ol) | 80 |
| Vertofix Coeur (commercial acetyl cedrene fraction) | 65 |
| (4'Z)-2,2-Dimethyl-5-(2'-methyloct-4'-enyl)-2,5-dihydrofuran (Example 2) | 20 |

At 2% (4'Z)-2,2-dimethyl-5-(2'-methyloctyl)tetrahydrofuran (example 2) conveyed to this woody unisex fragrance a floral freshness with a sparkling green-metallic effect that induced a reminiscence to violet leaf oil in the top note. In the heart note the fragrance became sweeter and warmer, more rosy, and the (4'Z)-2,2-dimethyl-5-(2'-methyloctyl)tetrahydrofuran pushed also the orris effect thereby enhancing the overall richness of the fragrance

EXAMPLE 6

Fruity-Marine Perfume Oil for Fabric Softener

| Compound/Ingredient | parts by weight 1/1000 |
|---|---|
| AZURONE ™ (7-(3-methylbutyl)-2H-1,5-benzodioxepin-3(4H)-one) at 10% in TEC* | 4 |
| Benzyl acetate | 20 |
| alpha-Damascone | 7 |
| Diethyl phthalate | 120 |
| Dihydromyrcenol | 50 |
| Dimethyl benzyl carbinyl acetate | 75 |

-continued

| Compound/Ingredient | parts by weight 1/1000 |
|---|---|
| Ethyl vanillin at 10% in DPG | 4 |
| Evernyl (methyl 2,4-dihydroxy-3,6-dimethylbenzoate) | 2 |
| Florhydral (3-(3'-isopropylphenyl)butanal) | 5 |
| (3Z)-Hex-3-en-1-ol | 3 |
| Hexyl salicylate | 55 |
| ISO E SUPER ™ (1-(2',3',8',8'-tetramethyl-1',2',3',4',5',6',7',8'-octahydronaphthalen-2'-yl)ethanone) | 80 |
| Kephalis (4-(1'-ethoxyvinyl)-3,3,5,5-tetramethylcyclohexanone) | 20 |
| Lilial (3-(4-tert-butylphenyl)-2-methylpropanal) | 55 |
| Linalool | 40 |
| Menthyl Diantilis (2-ethoxy-4-(methoxymethyl)phenol) | 7 |
| Neroline (2-ethoxy naphthalene) | 8 |
| Patchouli oil | 10 |
| PEONIL ™ (alpha-cyclohexylidene benzeneacetonitrile) | 100 |
| 2-Phenylethanol | 55 |
| Radjanol (2-ethyl-4-(2,2,3-trimethylcyclopent-3-enyl)but-2-en-1-ol) | 50 |
| SERENOLIDE ™ (2-(1'-(3",3"-dimethylcyclohexyl)ethoxy)-2-methylpropyl cyclopropanecarboxylate) | 80 |
| Verdyl acetate | 50 |
| 2,2-Dimethyl-5-(2'-methyloctyl)tetrahydrofuran (Example 2) | 100 |

*TEC = Triethyl citrate

At 10% 2,2-dimethyl-5-(2'-methyloctyl)tetrahydrofuran (example 2) rendered the odor more sweet, musky and powdery, and pushed the neroli effect with an additional fresh hesperidic boost, most noticeable in the heart accord. Thereby it brought additional volume to this composition, and a caressing and comforting feeling in the functional application of the perfume oil.

The invention claimed is:

1. A compound of formula (I)

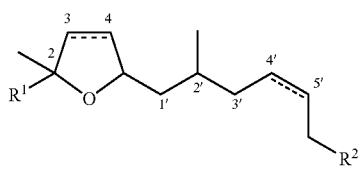

(I)

wherein $R^1$ is hydrogen or methyl;

$R^2$ is ethyl, propyl or isopropyl;

the bond between C-3 and C-4 is a single bond, or the dotted line together with the bond between C-3 and C-4 represents a double bond; and the bond between C-4' and C-5' is a single bond, or the dotted line together with the bond between C-4' and C-5' represents a double bond, either in (E)- or (Z)-configuration.

2. A compound according to claim 1 selected from the group consisting of:

(4'Z)-2,2-dimethyl-5-(2'-methyloct-4'-enyl)-2,5-dihydrofuran, 2,2-dimethyl-5-(2'-methyloctyl)tetrahydrofuran, (4'Z)-2-methyl-5-(2'-methyloct-4'-enyl)tetrahydrofuran, and, 2-methyl-5-(2-methyloctyl)tetrahydrofuran.

3. A fragrance composition comprising:

a) a compound according to claim 1; and b) a consumer product base, wherein the consumer product base is selected from the group consisting of: fine fragrance, household product, laundry product, body care product and cosmetic product.

4. A method of improving, enhancing or modifying a perfume composition or fragrance application comprising the step of:

incorporating an effective amount of a compound according to claim 1 in a base material.

5. A method of improving, enhancing or modifying a perfume composition or fragrance application comprising the step of:

incorporating an effective amount of a compound selected from the group consisting of:

(4'Z)-2,2-dimethyl-5-(2'-methyloct-4'-enyl)-2,5-dihydrofuran, 2,2-dimethyl-5-(2'-methyloctyl)tetrahydrofuran, (4'Z)-2-methyl-5-(2'-methyloct-4'-enyl)tetrahydrofuran, and, 2-methyl-5-(2-methyloctyl)tetrahydrofuran in a base material.

* * * * *